United States Patent

Bosland et al.

[11] 4,140,007
[45] Feb. 20, 1979

[54] SUSPENDED-SOLIDS METER

[75] Inventors: Steven C. Bosland, Enfield; William H. Kingston, Windsor Locks, both of Conn.

[73] Assignee: Combustion Engineering, Inc., Windsor, Conn.

[21] Appl. No.: 889,681

[22] Filed: Mar. 24, 1978

[51] Int. Cl.² .................................... G01N 15/06
[52] U.S. Cl. ................................................ 73/61.4
[58] Field of Search ................ 73/61.4, 61 R, 61.1 R, 73/53, 438, 439; 210/85, 90

[56] References Cited

U.S. PATENT DOCUMENTS

| | | | |
|---|---|---|---|
| 1,697,867 | 1/1929 | Haultain | 73/438 |
| 2,946,443 | 7/1960 | Schmidt | 73/439 X |
| 2,958,223 | 1/1960 | Hubby | 73/438 |
| 3,399,573 | 9/1968 | Ponsar | 73/438 |
| 3,896,660 | 7/1975 | Valentyik | 73/61.4 |
| 4,047,891 | 9/1977 | Schuetz | 73/32 R X |

Primary Examiner—Richard C. Quiesser
Assistant Examiner—Joseph W. Roskos
Attorney, Agent, or Firm—Joseph H. Born; Richard H. Berneike

[57] ABSTRACT

In order to determine the percentage of suspended solids in a slurry, a hollow tube is extended into a slurry tank in which the solids are kept in suspension by a mixer. The tube allows the liquid within it to be isolated from the action of the mixer, so the solids settle out of the tube. A pressure difference between points at the same elevation inside and outside of the tube is measured, and this gives a percent-solids indication in which error due to dissolved solids is negligible.

2 Claims, 1 Drawing Figure

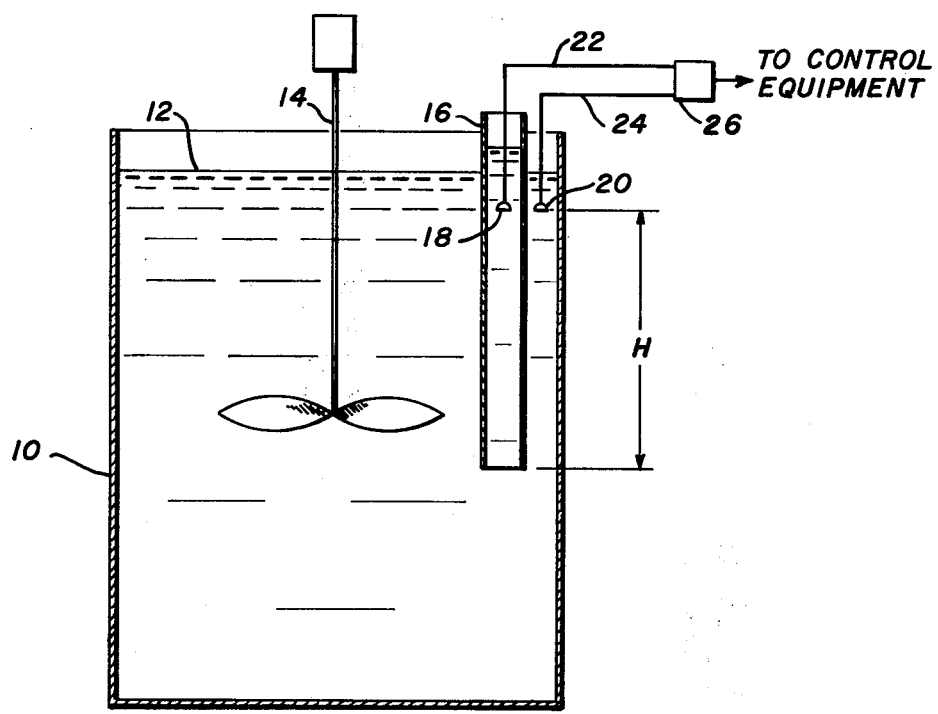

4,140,007

SUSPENDED-SOLIDS METER

BACKGROUND AND SUMMARY OF THE INVENTION

The present invention relates to determining the amount of solids present in a slurry. This determination is necessary in the operation of certain types of air-quality control systems in which a slurry is sprayed into fume-laden gases in order to remove certain pollutants. It is necessary for proper operation that the percentage of solids in the slurry remain within predetermined limits.

In the past, the percent-solids determination was made by measuring the density of the slurry. It was found that this method was not entirely satisfactory because the specific gravity of the slurry is affected not only by the presence of suspended solids but also by solids dissolved in the liquid. If the effect of dissolved solids were ignored, large inaccuracies would result because small changes in the specific gravity of the liquid portion of the slurry could appear to be large changes in the percentage of suspended solids. Thus, it was necessary to calibrate the instruments repeatedly in order to take into account the change in specific gravity of the "process liquid."

This recalibration problem was solved by Schuetz (U.S. Pat. No. 4,047,891), who suggested employing the process liquid in a bubbler pressure sensor in order to eliminate the effect of a change in process-liquid specific gravity. In one of the normal methods of testing specific gravity, the difference in pressure between two elevations in a container of liquid is sensed. The pressures are transmitted to a differential pressure sensor through two fluid lines through which fluid is continually fed into the container. Schuetz suggested using the process liquid as the fluid, and this had the result of virtually eliminating the effect of the process-liquid specific gravity on the percent-solids measurement. As can be seen in the drawings in the Schuetz Patent, which is hereby incorporated by reference, the process liquid used in the bubbler is taken from a thickener tank. The thickener tank is located outside the reaction tank in which the slurry that is to be used in the scrubber is contained. The process liquid from the thickener then flows through appropriate valving to the reaction tank, and in doing so it serves as the medium through which the pressure to be sensed is transmitted.

The present invention is an improvement over the Schuetz method in that the method and apparatus of the present invention permit the measurement to be carried out more simply. In addition, they avoid the possibility that operator error could permit the slurry to back up through the wrong tubes and thereby damage equipment. Furthermore, they ensure that the properties of the process liquid used in the measurement are as close as possible to those of the process liquid that is actually in the reaction tank.

The present invention is a method and apparatus for measuring the suspended-solids content of a liquid in which the suspended solids have a tendency to settle. A vessel for containing liquids is provided, as are means for agitating liquid contained in the vessel. The agitating means are provided so that any solids in the liquid remain in suspension. A tube extends into the vessel interior, and the tube is hollow and open at its lower end so that it will contain some liquid when the vessel contains liquid up to a level high enough to reach the tube. This tube isolates the liquid contained in it from the action of the agitation means, so the solids in the tube are allowed to settle out. The difference between the pressures at two points of equal elevation, one inside and one outside the tube, is sensed, and this gives an accurate indication of the suspended-solids content of the liquid in the vessel.

BRIEF DESCRIPTION OF THE DRAWING

These and further features and advantages of the present invention are described in connection with the drawing, which is a somewhat diagrammatical rendering of the apparatus of the present invention.

DETAILED DESCRIPTION OF THE PREFERRED EMBODIMENT

The FIGURE shows a vessel 10 that contains a slurry up to a level 12. Appropriate agitating means are suggested by member 14, a diagrammatic respresentation of a mixer. Though a mixer is not necessary, some agitating means is required, even if it only comprises an inlet and outlet that set up the currents in the slurry, so that the solids suspended in the slurry will not settle out. A hollow tube 16 is shown extending into the vessel, and its bottom end is open so that liquid can enter it. As will be appreciated from the description below, the liquid inside the tube 16 will in general have a specific gravity lower than that of the rest of the slurry, and it is for this reason that the level inside the tube is shown as being higher than the general level 12. Appropriate pressure sensors 18 and 20 are located at equal elevations in the liquid, one being inside the tube 16 and the other being outside it. Both sensors 18 and 20 are suspended at a vertical distance H above the bottom of the tube 16. Pressure signals are shown being transmitted by means of lines 22 and 24 to an appropriate difference-indicating means 26, the output of which is set to whatever control or indicating equipment is desired. Sensors 18 and 20 could be transducers that send electrical signals to a differential amplifier included as part of element 26. Alternatively, elements 18 and 20 could be nothing more than the inlets to fluid conduits represented by elements 22 and 24, and element 26 would then be a differential pressure transducer. Whether these or other means are used, the essence is that some means be provided for sensing the difference in pressure between points of equal elevation in a liquid, one being inside and the other being outside the tube 16.

In operation, vessel 10 would typically be the reaction tank of an air-quality control system. Slurry would be contained in the tank and would be continuously withdrawn to be sprayed into flue gases, the spray passing through the flue gases and falling back into the reaction tank. The makeup of the slurry in the reaction tank is continually controlled by adding water and reactants and bleeding off some of the slurry. This control would be performed at least partially in response to the signal from the means for sensing pressure differences. The mixer 14 keeps the solids in the slurry in suspension, so the solids are homogeneously dispersed in the slurry. Within the tube 16, however, the currents caused by the mixer 14 are not present, and the solids can settle out, leaving only the process liquid. As a result, the pressure at sensor 18 is equal to the pressure at the bottom of the tube, in inches of water, diminished by the product of the vertical distance H and the specific gravity of the process liquid. The pressure at sensor 20, on the other hand, is equal to the pressure at the bottom of the tube 16 diminished by the product of the vertical distance H and the specific gravity of the slurry. Thus, the output signal from the element 26 is proportional to the difference between the specific gravity of the slurry and the specific gravity of the process liquid:

$$\Delta P = (P_O - H \cdot SG_{PL}) - (P_O - H \cdot SG_{SL}) \qquad (1)$$

$$\Delta P = H(SG_{SL} - SG_{PL}), \qquad (2)$$

where $\Delta P$ is the pressure difference in inches of water indicated by the sensors 18 and 20, $P_O$ is the pressure at the bottom of the tube 16, H is the vertical distance in inches between the bottom of the tube and the sensors, $SG_{SL}$ is the specific gravity of the slurry, and $SG_{PL}$ is the specific gravity of the process liquid.

Solids content can be inferred from the $\Delta P$ indication and equation (2) by taking advantage of the fact that the difference in specific gravities is approximately equal to the difference between unity and the specific gravity that the slurry would have if the process liquid were pure water:

$$SG_{SL} - SG_{PL} \approx SG_{W/SS} - 1, \qquad (3)$$

where $SG_{W/SS}$ is the specific gravity that the slurry would have if there were no dissolved solids in the process liquid. By using equations (2) and (3), one can determine $SG_{W/SS}$ from the $\Delta P$ indication, and it is a simple matter to determine solids content from $SG_{W/SS}$:

$$SG_{W/SS} = \frac{1}{\frac{r}{SG_{SS}} + \frac{1-r}{1.00}} \qquad (4)$$

$$r = \left(\frac{SG_{SS}}{SG_{W/SS}} - SG_{SS}\right)\frac{1}{1 - SG_{SS}} \qquad (5)$$

$$= \frac{SG_{SS}}{SG_{SS} - 1} \cdot \frac{\Delta P}{\Delta P + H}, \qquad (6)$$

where $SG_{SS}$ is the specific gravity of the solids and r is the fraction of suspended solids in the slurry by weight.

It is to be noted that this method assumes as an equality the approximation given by Equation (3), so there is still some inaccuracy introduced by the method. However, this inaccuracy is quite small, and it compares favorably with the method in which the solids content is inferred from the specific gravity of the slurry alone without consideration of process-liquid specific gravity.

Consider, for example, a slurry that has 10% undissolved solids suspended in a process liquid with a specific gravity of 1.02. Assuming a suspended-solids specific gravity of 2.5, the present invention will indicate a suspended-solids content of 10.05%. If the suspended-solids content were to be inferred merely from the specific gravity of the slurry, on the other hand, an assumption of no dissolved solids would yield an indication of 12.9%. Clearly, the inaccuracy introduced by Equation (3) is more than made up for by the elimination of the error inherent in the other method.

It can be appreciated that the foregoing description discloses a very simple method of measuring solids content. In addition is simplicity, increased accuracy is also afforded because the process liquid used in the measurement is the same liquid that is in the vessel at the very instant of measuring. Furthermore, since the tube is located in the vessel, any inaccuracy that could be caused by a difference in temperature between the process liquid used for measurement and the process liquid actually in the tank is eliminated. Finally, since the method and apparatus of the present invention do not use a bubbler, there is no possibility of damage resulting from slurry backing up into the equipment.

What is claimed is:

1. An apparatus for measuring the suspended-solids content of a liquid in which suspended solids have a tendency to settle, comprising:
   a. a vessel for containing the liquid;
   b. means for agitating the liquid contained in the vessel in order to keep any solids therein in suspension;
   c. a hollow tube open at its lower end and extending into the vessel interior, the tube thereby containing some liquid when the vessel contains liquid to a level high enough to reach the tube, for isolating the liquid contained in the tube from the action of the agitating means and thereby allowing solids to settle out of the liquid in the tube; and
   d. means for sensing the pressure difference between two points of equal elevation within the liquid contained in the vessel, one of the points being inside the tube and the other being outside the tube, the sensing means thereby indicating the suspended-solids content of the liquid in the vessel.

2. A method of measuring the suspended-solids content of a liquid in which the solids have a tendency to settle, comprising the steps of:
   a. agitating the liquid in order to keep any solids therein in suspension;
   b. providing a hollow tube in the liquid, the tube thereby containing some of the liquid and isolating it from agitation, solids thereby being allowed to settle out of the liquid in the tube; and
   c. sensing the pressure difference between two points of equal elevation in the liquid, one point being inside the tube and the other being outside the tube.

* * * * *